United States Patent [19]

Carroll et al.

[11] Patent Number: 5,521,698
[45] Date of Patent: May 28, 1996

[54] ANALYSIS SYSTEM

[75] Inventors: Charles E. Carroll, Kingston, N.H.;
Garry C. Kunselman, Stow, Mass.;
Arthur E. Tobey, Salem, N.H.;
Richard J. Belmore, East Bridgewater, Mass.

[73] Assignee: Thermo Jarrell Ash Corporation, Franklin, Mass.

[21] Appl. No.: 377,127

[22] Filed: Jan. 23, 1995

Related U.S. Application Data

[63] Continuation-in-part of Ser. No. 191,395, Feb. 2, 1994.

[51] Int. Cl.$^6$ .......................... G01N 21/00; G01N 21/67
[52] U.S. Cl. ................... 356/70; 356/73; 356/313
[58] Field of Search ........................ 356/70–73, 313, 356/440

[56]  References Cited

U.S. PATENT DOCUMENTS

| | | | |
|---|---|---|---|
| 3,526,127 | 9/1970 | Sarkis | 356/70 X |
| 3,645,628 | 2/1972 | Bojic et al. | 356/313 |
| 4,367,043 | 1/1983 | Sweet et al. | 356/440 X |
| 4,469,441 | 9/1984 | Bernier et al. | 356/316 |
| 4,618,769 | 10/1986 | Johnson et al. | 356/440 |
| 5,141,314 | 8/1992 | Belmore et al. | 356/313 |
| 5,207,905 | 5/1993 | O'Brien et al. | 210/274 |
| 5,278,629 | 1/1994 | Schlager et al. | 356/313 |

FOREIGN PATENT DOCUMENTS

| | | | |
|---|---|---|---|
| 63-66342 | 11/1988 | Japan | 356/70 |

OTHER PUBLICATIONS

Detect Auto Labs, Inc., "Blood Test for Your Engine", 1988.
Garry, *Nicolet Instrument Corporation*, "Applied Interpretation of FT–IR Oil Analysis Results for Improving Predictive Maintenance Programs", 1991.

*Primary Examiner*—Vincent P. McGraw
*Assistant Examiner*—K. P. Hantis
*Attorney, Agent, or Firm*—Fish & Richardson

[57]  ABSTRACT

An analytical system for analyzing a liquid sample that includes structure defining an analysis region with an inlet and an outlet, a spectrometer system disposed in sensing relation to the analysis region, structure defining a sample inlet port, and structure connecting the sample inlet port to the inlet of the analysis region. The analysis region includes sample excitation apparatus with a pair of spaced metal electrodes, one of the electrodes having an upper surface in spaced juxtaposition to the other electrode and passage structure connected to the inlet of the analysis region, and the other electrode having a lower surface of annular configuration in spaced juxtaposition to the upper surface of the one electrode. The one metal electrode is disposed with the passage structure extending to an outlet port in its upper surface, and that electrode includes structure in the upper surface defining a plurality of channels extending away from the outlet port for discharge of excess quantities of a liquid sample to be analyzed that has been flowed through the passage structure. Control structure flows a sample to be analyzed from the sample inlet port through the analysis region, and output structure responsive to the spectrometer system provides output data as a function of the liquid sample flowed into the sample excitation apparatus.

23 Claims, 3 Drawing Sheets

ANALYSIS SYSTEM

This application is a continuation-in-part of U.S. Ser. No. 08/191,395, filed Feb. 2, 1994.

This invention relates to analysis systems, and more particularly to apparatus and processes for analyzing liquid samples.

BACKGROUND OF THE INVENTION

Analyses of constituents of oils for lubricating machinery provide information on current conditions of the machinery and may identify problems which may require costly repair if not corrected. Analytical services have been provided through the use of a kit type service in which a sample of engine oil is mailed to an analysis laboratory and a report is furnished after the laboratory conducts an analysis using conventional analysis equipment such as a polychromater with rotatable carbon electrodes. Improved analysis systems and procedures are disclosed in co-pending application Ser. No. 08/191,395, filed Feb. 2, 1994, and entitled "ANALYSIS SYSTEM" the disclosure of which is expressly incorporated herein by reference. While the system and procedures disclosed in that application are suitable for a variety of liquid samples, certain liquid samples such as diesel engine oils, may be of high viscosity, and also may include large amounts of significant constituents such as 2,000 ppm zinc.

SUMMARY OF THE INVENTION

In accordance with one aspect of the invention, there is provided an analytical system for analyzing a liquid sample that includes structure defining an analysis region with an inlet and an outlet, a spectrometer system disposed in sensing relation to the analysis region, structure defining a sample inlet port, and structure connecting the sample inlet port to the inlet of the analysis region. The analysis region includes sample excitation apparatus with a pair of spaced metal electrodes, one of the electrodes having an upper surface in spaced juxtaposition to the other electrode and passage structure connected to the inlet of the analysis region, and the other electrode having a lower surface of annular configuration in spaced juxtaposition to the upper surface of the one electrode. The one metal electrode is disposed with the passage structure extending to an outlet port in its upper surface, and that electrode includes structure in the upper surface defining a plurality of channels extending away from the outlet port for discharge of excess quantities of a liquid sample to be analyzed that has been flowed through the passage structure. Control structure flows a sample to be analyzed from the sample inlet port through the analysis region, and output structure responsive to the spectrometer system provides output data as a function of the liquid sample flowed into the sample excitation apparatus.

The pair of spaced metal electrodes have structures which encourage random spark emissions across the opposing surfaces of the electrodes and reduces "hot spots" on the surfaces. As a result, the surface of the electrodes are maintained at lower temperatures during the analysis operation and the possibility for "burned-on" residue of the liquid sample at "hot spots" on the surface of the electrodes is reduced. The channeled surface of the lower electrode provides a number of discharge points at which the liquid sample covering these points can be spectroemissively excited. The annular structure of the upper electrode is "tube-like" in a particular embodiment, and avoids an undesirable single discharge point and provides a larger surface area from which spark emissions are generated further promoting the random sampling of the liquid sample being analyzed. Thus, the accuracy and sensitivity of the spectroanalysis of the liquid sample is improved and is less sensitive to the amount of the sample which flows over the upper surface of the lower electrode.

In accordance with another aspect of the invention, there is provided an analytical system for analyzing a liquid sample that includes structure defining an analysis region having an inlet and an outlet, a spectrometer system disposed in sensing relation to the analysis region, structure defining a sample inlet port, structure connecting the sample inlet port to the inlet of the analysis region, the structure connecting the sample inlet port to the inlet of the analysis region including a sample transport tube and structure for introducing gas bubbles into the sample to be analyzed for flow with the sample through the transport tube to the analysis region. The analysis region includes sample excitation apparatus with a pair of spaced metal electrodes, one of the electrodes having an upper surface in spaced juxtaposition to the other electrode and passage structure connected to the inlet of the analysis region, and the other electrode having a lower surface in spaced juxtaposition to the upper surface of the one electrode, the one metal electrode being disposed with the passage structure extending to an outlet port in its the upper surface. Control structure flows a sample to be analyzed from the sample inlet port through the analysis region, and output structure responsive to the spectrometer system for providing output data as a function of the liquid sample flowed into the sample excitation apparatus.

Preferably, the structure connecting the sample inlet port to the inlet of the analysis region that includes a sample flow tube and an adjacent tube for introducing gas bubbles into the sample to be analyzed for flow with the sample through the transport tube to the analysis region. In a particular embodiment, the gas flow tube is disposed concentrically with the sample transport tube and their ports are disposed adjacent one another for submergence in the liquid sample to be analyzed so that, during a cleaning interval, gas bubbles may be flowed through the sample inlet passage concurrently with the sample liquid or a cleaning liquid for cleaning the inlet tube and other regions of the analysis sample flow path.

Particular embodiments may include one or more of the following features. The spectrometer system includes entrance slit structure, exit slit structure composed of a plurality of exit slit regions, and radiation dispersing structure for dispersing radiation passing through the entrance slit structure into a spectrum for application to the exit slit regions. The metal electrode contains at least ninety-nine percent of a particular metal, for example, silver. The sample excitation apparatus is disposed in an enclosed chamber that has an outlet port across which filter structure is disposed, and structure for flowing gas from the chamber through the filter structure for exhaust outside the housing structure. The sample excitation apparatus includes a pair of trigger electrodes disposed in spaced relation to the metal electrodes in the analysis region such that the breakdown of the gap between the trigger electrodes is adapted to generate ultraviolet radiation to preionize the gap between the main electrodes. The control structure for flowing a sample includes a pump that has forward and reverse modes of operation, with the control structure being adapted to operate the pump in a reverse flow mode during a first part of a spectrometer analysis cycle to remove excess sample material from the analysis region and then in a relatively low forward flow rate mode during a second part of the spectrometer analysis cycle. The system includes housing structure in which the spectrometer system and the analysis region is disposed, and wheel structure on which the housing structure is mounted so that the analysis system is relatively mobile.

In accordance with another aspect, there is provided a process for analyzing liquid sample material such as a lubricating oil comprising the steps of providing structure defining an analysis region with a polychromater system disposed in sensing relation to the analysis region, the polychromator system including entrance slit structure, exit slit structure composed of a plurality of exit slit regions, and radiation dispersing structure for dispersing radiation passing through the entrance slit structure into a spectrum for application to the exit slit regions, flowing a liquid sample to be analyzed through a sample flow path into the analysis region at a first flow rate, flowing gas bubbles concurrently with the sample for cleaning the sample flow path, reversing the flow direction to remove excess liquid sample from the analysis region, resuming flow in the forward direction at a low flow rate and concurrently subjecting the liquid sample in the analysis region to an electric discharge to excite the liquid sample to spectroemissive levels for sensing by the polychromator system.

BRIEF DESCRIPTION OF THE DRAWINGS

Other features and advantages of the invention will be seen as the following description of a particular embodiment progresses, in conjunction with the drawings, in which.

DESCRIPTION OF THE PARTICULAR EMBODIMENT

Figure 1:
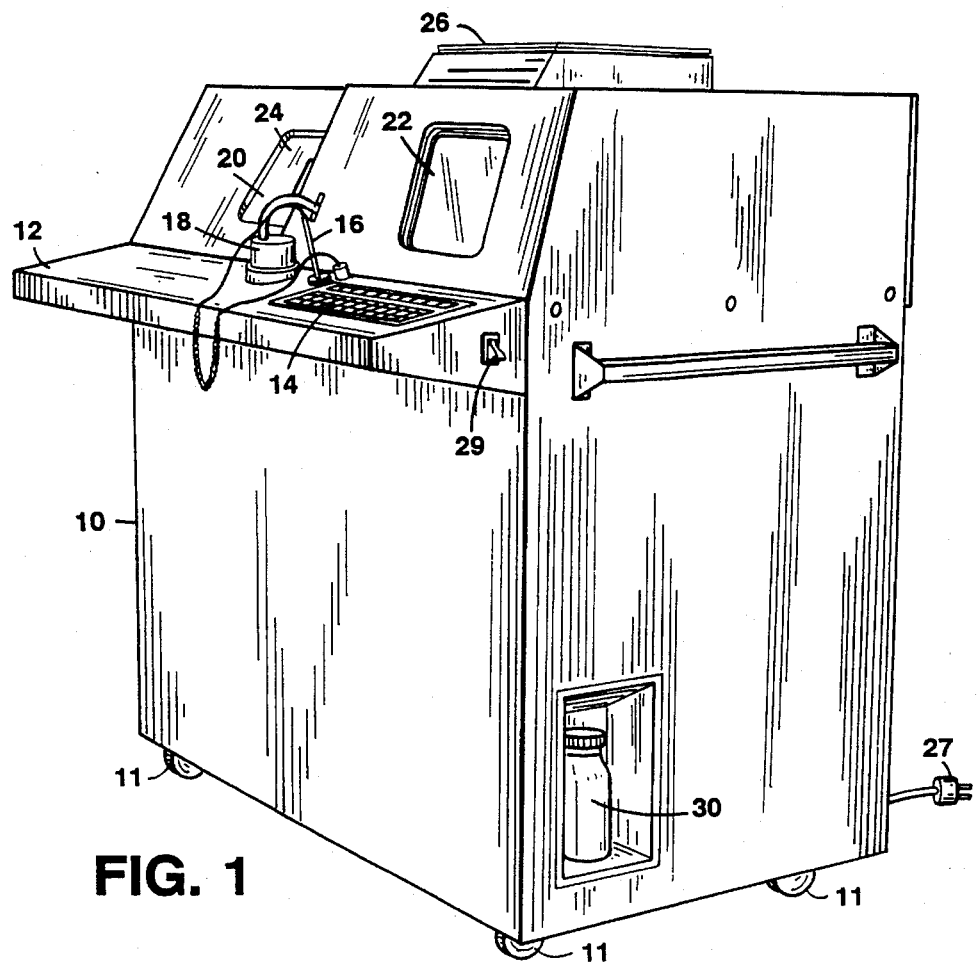
FIG. 1 is a perspective view of an analysis system in accordance with the invention.

The system shown in FIG. 1 includes a mobile housing 10 mounted on wheels 11 with shelf 12 on which is mounted control keyboard 14, light pen-type bar code reader 16, and oil sample receiver 18. Coupled to sample receiver 18 is inlet assembly 20. Mounted in the console above surface 12 are display 22 and arc stand chamber access door 24. A second output device in the form of printer 26 is disposed on top of housing 10; 115 volt line cord 27 supplies electrical power to the system under the control of switch 29; and waste container 30 is disposed in the end wall. Controller 32 (FIG. 2) is mounted in housing 10 behind display 22. This system is of the general type shown and described in co-pending application Ser. No. 08/191,395 entitled "ANALYSIS SYSTEM", filed Feb. 2, 1994, the disclosure of which is expressly incorporated herein by reference.

Figure 2:
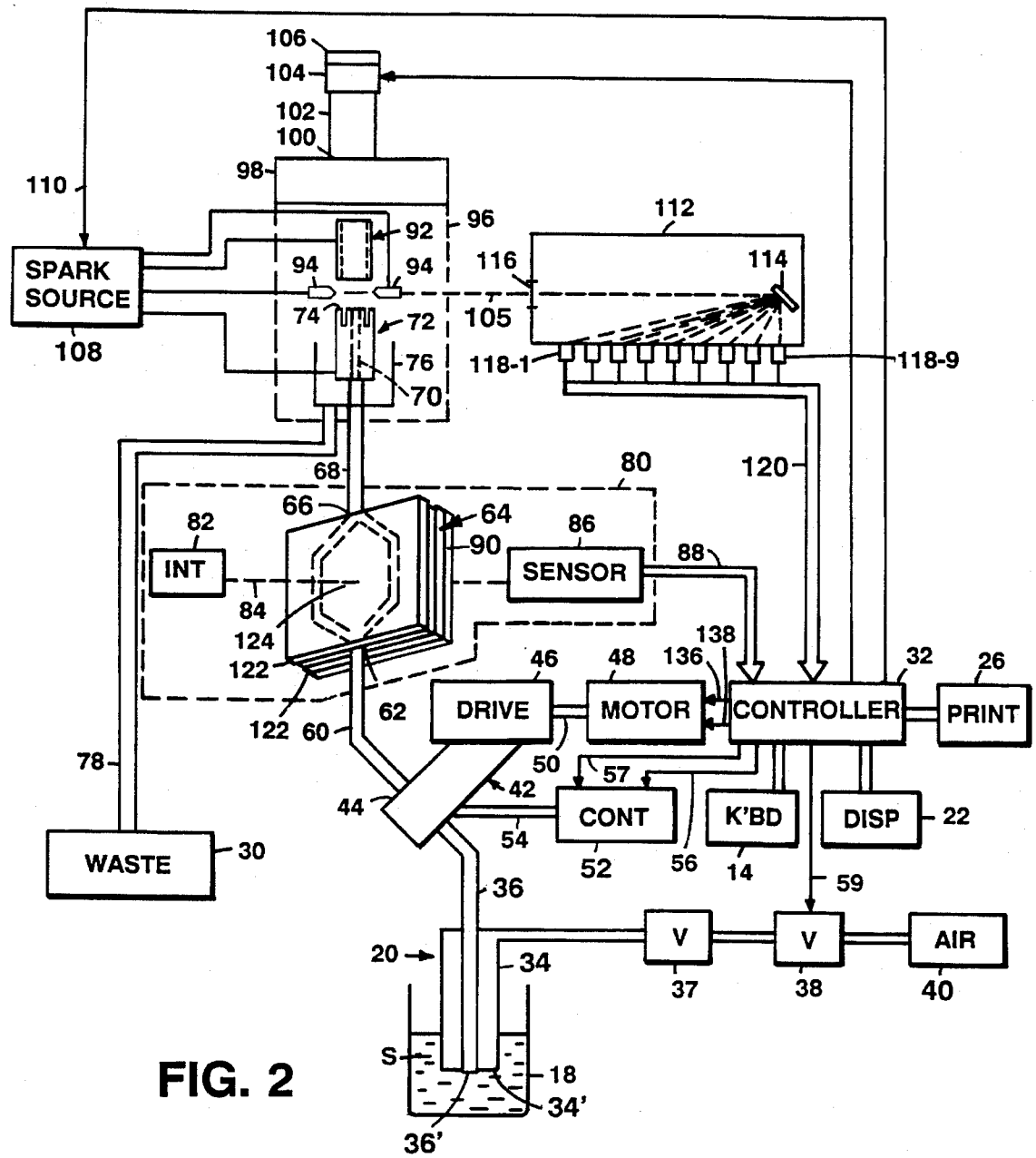
FIG. 2 is a block diagram of the system shown in FIG. 1, including diagrammatic showings of the sample flow path and the analysis regions.

With reference to FIG. 2, sample input assembly 20 includes stainless steel outer tube 34 that has an inner diameter of about four millimeters, and Teflon inner tube 36 that has an outer diameter of about three millimeters and an inner diameter of about 1.5 millimeters. Coupled to outer tube 34 via adjustable needle valve 37 and solenoid control valve 38 is a source 40 of air at a pressure of about 10–12 psi. Tubes 34 and 36 have ports 34' and 36' at their lower ends that are in substantial alignment and are arranged for insertion into the liquid sample S to be analyzed that is disposed in sample container 18. Coupled to the other end of inner tube 36 is metering pump 42, (Model Q1CKCLF Fluid Metering, Inc., Oyster Bay, N.Y.). Metering pump 42 includes a piston and cylinder assembly 44 that is mounted for pivoting movement on rotatable drive assembly 46 which is coupled to stepper motor 48 by timing belt 50. Air cylinder 52 is connected to assembly 44 by link 54 and receives control signals over lines 56, 57 from controller 32 to select a pumping volume of pump 42. A control signal over line 56 places the pump 42 in a low flow position (about 0.5 milliliter per minute) while a signal over line 57 places the pump system in a high flow position (about five milliliters per minute).

The liquid sample is pumped by pump 42 over line 60 into FTIR (infrared) system 80, which may be a Nicolet Impact 400 system. The sample is pumped to the inlet 62 of FTIR flow-through cell 64 and from outlet 66 over line 68 to flow through passage 70 of silver spark source electrode 72. The liquid sample pumped by pump 42 through cell 64 to electrode 72 flows over the top surface 74 of electrode 72 and into well 76 for transfer over line 78 to waste bottle 30.

FTIR system 80 includes an interferometer 82 that directs radiation beam 84 through flow cell 64 to sensor 86 which applies output signals over line 88 to controller 32. Coupled to cell 64 is heater 90 which is adapted to maintain cell 64 at a temperature of about 155° F. during the analysis operation.

A spark source unit 108 is provided for exciting the oil sample under analysis. Silver upper and lower main electrodes 72, 92 and trigger electrodes 94 are housed in chamber 96 having access door 24 (FIG. 1) in its front wall. As shown in FIG. 2, chamber 96 has an activated charcoal and particulate filter 98 disposed across exhaust port 100 in a rear chamber wall with tube 102 coupling port 100 to exhaust fan 104 and exhaust port 106 mounted in the rear wall of housing 10. Spark source unit 108 of the type shown in Belmore, U.S. Pat. No. 5,141,314 (the disclosure of which is expressly incorporated herein by reference) is mounted in the lower part of housing 10. Spark source unit 108 receives control signals over lines 110 from controller 32, and energizes trigger electrodes 94 and main electrodes 72, 92 to generate sparks across the electrode gap to excite the oil sample to be analyzed to spectroemissive levels.

Optically coupled to the gap between electrodes 72, 92 is a 0.75 meter, 9 channel polychromater unit 112 that includes radiation dispersing grating 114, entrance slit structure 116, and nine exit slit structures with corresponding photomultiplier tubes 118 for generating output signals over lines 120 for application to controller 32. The photomultiplier tubes 118 are positioned to sense elementary aluminum, copper, iron, potassium, phosphorous, zinc, silicon, chromium, and tin. The FTIR system 80 provides signals over lines 88 for analysis of sample constituents such as glycol, water, fuel and soot.

FTIR flow through cell 64 includes two potassium bromide plates 122 spaced about 0.1 millimeter apart to provide a flow through sensing region 124 in which the oil sample to be analyzed is disposed and through which beam 84 is passed.

Figure 3:
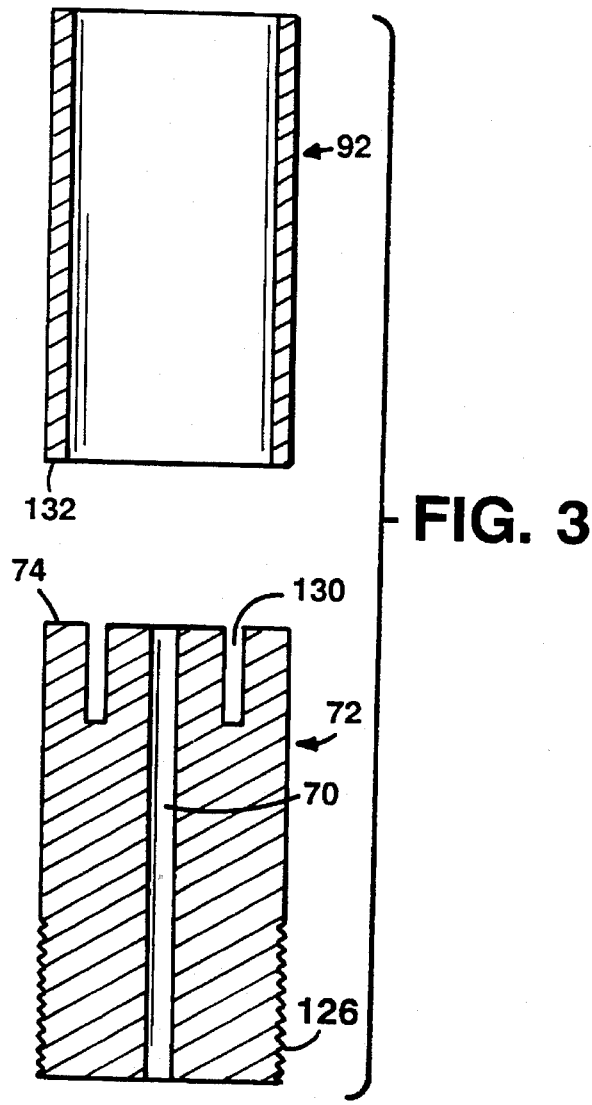
FIG. 3 is a side sectional view of the upper and lower arc stand electrodes employed in the spectroscopy component of the system shown in FIG. 1.
Figure 4:
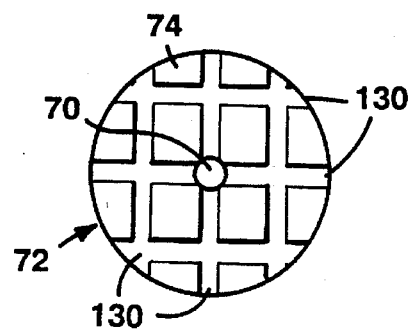
FIG. 4 is a top view of the lower arc stand electrode shown in FIG. 3.
Figure 5:
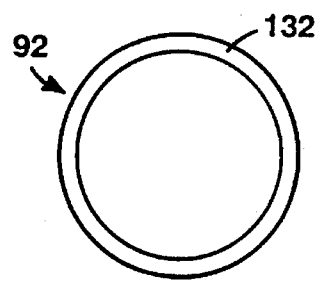
FIG. 5 is a bottom view of the upper arc stand electrode shown in FIG. 3.

Referring to FIG. 3, a side sectional view of the spaced 99.9% pure silver spark electrodes 72, 92 is shown; FIG. 4 is a top view of electrode 72; and FIG. 5 is a bottom view of electrode 92. Each electrode 72, 92 has a diameter of about 0.6 centimeter and a length of about 1.2 centimeters. Electrode 72 has threaded section 126 remote from the electrode gap. Tubular upper electrode 92 is secured with set screws. Through passage 70 of lower electrode 72 has a diameter of about one millimeter with upper surface 74 having a rectangular array of nine slots 130, each of which has a width of about ½ millimeter and a depth of about ½ centimeter formed thereon. The electrode 92 has an annular wall 132 of about 0.25 millimeter thickness.

Trigger electrodes 94 are thoriated tungsten pointed rods, have diameters of 1.5 millimeters, and are disposed in spaced alignment, about two centimeters to the rear of electrodes 72, 92 and perpendicular to the main electrodes. Spark source unit 108 breaks down the trigger gap and the resulting ultraviolet radiation preionizes the main gap and assists in the breakdown of that gap with a spark striking from annular wall 132 to electrode surface 74, the spark exciting the oil or other liquid sample on surface 74 to spectroemissive levels. Triggering signals on line 110 are generated at a 120 hertz repetition rate, with each main spark triggered for a duration of about 800 microseconds and having a magnitude of about 25 amperes.

In system use, sample S of the oil (or other liquid) to be analyzed in sample container 18 is sucked through inlet assembly 20 by pump 42 for flow through FTIR sensing region 124 of FTIR system 80 and then through passage 70 of lower silver electrode 72 for flow to upper surface 74 and overflow along slots 130 and over line 78 to waste bottle 30.

Figure 6:
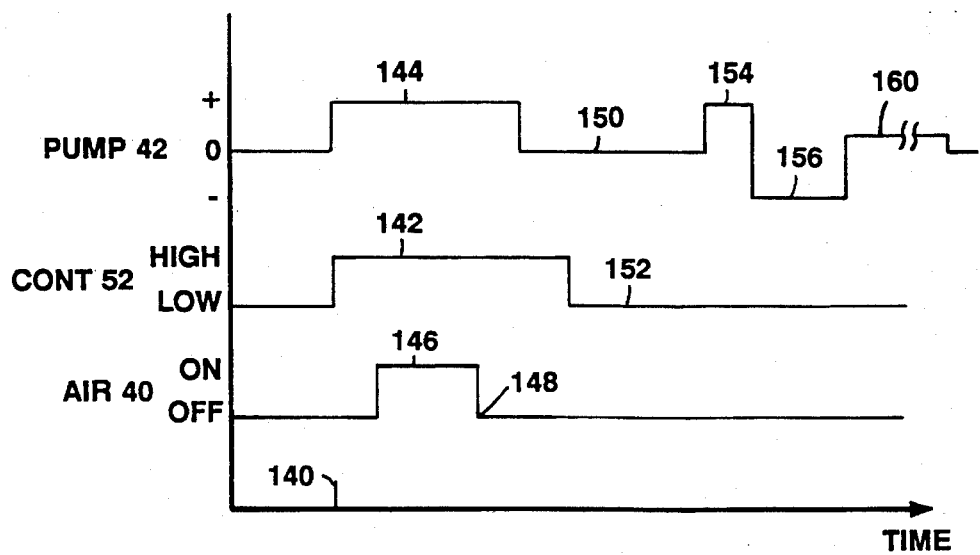
FIG. 6 is a timing diagram indicating a sequence of operations with the system of FIG. 1.

In an analysis sequence, as indicated in FIG. 6, sample S to be analyzed is placed in sample container 18 and the tips of tubes 34 and 36 of input assembly 20 are submerged in the sample S. Controller 32 sets pump rate selector 52 in its high volume position in response to a signal on line 57 and solenoid valve 38 is opened in response to signal on line 59 to flow air through outer tube 34 produce bubbles in the sample S which are drawn by pump 42 for flow through sensing region 124 and electrode passage 70, the interposed air bubbles providing a scouring action that enhances the removal of the prior sample traces from the flow path.

With reference to FIG. 6, system controller 32, at the start 140 of an analysis cycle, sets pump controller 52 in high flow rate position 142 in response to a signal on line 57; operates pump drive 46 in the forward direction as indicated in interval 144 in response to a signal on line 136 to provide a flow rate of about 5 milliliters per minute of the sample; and opens air valve 38 in response to a signal on line 59, as indicated at interval 146 to provide a flow of air bubbles into sample S which are sucked up through Teflon tube 36 to enhance the cleaning and scouring action and to reduce sample carryover. Controller 32 closes the air valve 38 at interval 148 and stops pump motor 48 about fifteen seconds later at interval 150 for an FTIR sample interval of about 30 seconds duration during which radiation beam 84 from interferometer 82 is passed through the sample cell 64 for detection by sensor 86. During this interval, air cylinder 52 is operated in response to a signal on line 58 to shift the pump assembly 44 to the lower speed position as indicated at interval 152. Pump motor 48 re-energizes pump 42 in the forward direction for a positive low flow rate interval 154 (a flow rate of about 0.5 milliliter per minute with no air flow) to flow the sample to be analyzed through inlet passage 70 of electrode 72 where it overflows into chamber 76 and into waste bottle 30. Motor 48 is then energized to place pump 42 in the reverse direction in response to a signal on line 138 from controller 32 to provide a slow reverse flow interval 156 of about fifteen seconds duration. Excess sample S is sucked from the upper surface 74 of electrode 72 followed by an analysis interval 160 (of at least about thirty seconds duration—about fifteen seconds preburn and about fifteen seconds integration per burn) (and which may include multiple burns) during which sample S is flowed at a rate of about 0.1 milliliter per minute through passage 70 and slots 130. During this flow period, electrodes 72, 92 are energized by spark source 108 to excite the oil sample to spectroemissive levels and to produce radiation beam 105 for sensing by polychromater unit 112.

The system allows analysis of a variety of liquid samples, including oils such as diesel fuels or other oils which may includes substantial quantities of contaminants and other constituents; and minimizes cross contamination. The electrode configuration provides good dispersion of sparks while permitting relatively large sample flow rates which contribute to the cooling of the lower electrode 72.

While a particular embodiment of the invention has been shown and described, various modifications will be apparent to those skilled to those in the art, and therefore, it is not intended that the invention be limited to the disclosed embodiment, or to details thereof, and departures may be made therefrom within the spirit and scope of the invention.

What is claimed is:

1. An analytical system for analyzing a liquid sample comprising structure defining an analysis region having an inlet and an outlet, a spectrometer system disposed in sensing relation to said analysis region, structure defining a sample inlet port, structure connecting said sample inlet port to said inlet of said analysis region, said analysis region including sample excitation apparatus with a pair of spaced metal electrodes, one of said electrodes having an upper surface in spaced juxtaposition to said other electrode and passage structure connected to said inlet of said analysis region, and the other electrode having a lower surface of annular configuration in spaced juxtaposition to said upper surface of said one electrode, said one metal electrode being disposed with said passage structure extending to an outlet port in its said upper surface, said one electrode including structure in said upper surface defining a plurality of channels extending away from said outlet port for discharge of excess quantities of a liquid sample to be analyzed that has been flowed through said passage structure, control structure for flowing a sample to be analyzed from said sample inlet port through said analysis region, and output structure responsive to said spectrometer system for providing output data as a function of the liquid sample flowed into said sample excitation apparatus.

2. The system of claim 1 wherein said structure connecting said sample inlet port to said inlet of said analysis region includes a sample transport tube and structure for introducing gas bubbles into the sample to be analyzed for flow with the sample through said transport tube to said analysis region.

3. The system of claim 2 wherein said structure for introducing gas bubbles includes a supplemental tube disposed concentrically with said sample transport tube and said tubes have ports disposed adjacent one another for submergence in the liquid sample to be analyzed so that, during a cleaning interval, gas bubbles may be flowed through said sample transport tube concurrently with the sample or cleaning liquid for cleaning said sample transport tube.

4. The system of claim 1 wherein said spectrometer system includes entrance slit structure, exit slit structure composed of a plurality of exit slit regions, and radiation dispersing structure for dispersing radiation passing through said entrance slit structure into a spectrum for application to said exit slit regions.

5. The system of claim 1 wherein each said metal electrode contains at least ninety-nine percent of a particular metal.

6. The system of claim 5 wherein said particular metal of each said electrode is silver.

7. The system of claim 1 wherein said sample excitation apparatus is disposed in an enclosed chamber, said chamber having an outlet port across which filter structure is disposed, and structure for flowing gas from said chamber through said filter structure for exhaust outside said system.

8. The system of claim 1 wherein said sample excitation apparatus includes a pair of trigger electrodes disposed in spaced relation to said metal electrodes in said analysis region such that the breakdown of the gap between said trigger electrodes is adapted to generate ultraviolet radiation to preionize the gap between said main electrodes.

9. The system of claim 1 wherein said control structure for flowing a sample includes a pump that has forward and reverse modes of operation, and said control structure operates said pump in a reverse flow mode during a first part of a spectrometer analysis cycle to remove excess sample material from said analysis region and then in a relatively low forward flow rate mode during a second part of said spectrometer analysis cycle.

10. The system of claim 9 wherein said system includes housing structure in which said analysis region and said spectrometer system are disposed, said sample excitation apparatus is disposed in an enclosed chamber, said chamber having an outlet port across which filter structure is disposed, and structure for flowing gas from said chamber through said filter structure for exhaust outside said housing structure.

11. The system of claim 10 wherein said spectrometer system includes entrance slit structure, exit slit structure composed of a plurality of exit slit regions, and radiation dispersing structure for dispersing radiation passing through said entrance slit structure into a spectrum for application to said exit slit regions.

12. The system of claim 11 and further including wheel structure on which said housing structure is mounted so that said analysis system is relatively mobile.

13. The system of claim 12 wherein each said metal electrode contains at least ninety-nine percent of a specific metal.

14. The system of claim 13 wherein said specific metal is silver.

15. An analytical system for analyzing a liquid sample comprising structure defining an analysis region having an inlet and an outlet, a spectrometer system disposed in sensing relation to said analysis region, structure defining a sample inlet port, structure connecting said sample inlet port to said inlet of said analysis region, said structure connecting said sample inlet port to said inlet of said analysis region including a sample transport tube and structure for introducing gas bubbles into the sample to be analyzed for flow with the sample through said sample transport tube to said analysis region, said analysis region including sample excitation apparatus with a pair of spaced metal electrodes, one of said electrodes having an upper surface in spaced juxtaposition to said other electrode and passage structure connected to said inlet of said analysis region, and the other electrode having a lower surface in spaced juxtaposition to said upper surface of said one electrode, said one metal electrode being disposed with said passage structure extending to an outlet port in its said upper surface, control structure for flowing a sample to be analyzed from said sample inlet port through said passage structure and said outlet port, and output structure responsive to said spectrometer system for providing output data as a function of the liquid sample flowed into said sample excitation apparatus.

16. The system of claim 15 wherein said spectrometer system includes entrance slit structure, exit slit structure composed of a plurality of exit slit regions, and radiation dispersing structure for dispersing radiation passing through said entrance slit structure into a spectrum for application to said exit slit regions.

17. The system of claim 15 wherein said structure for introducing gas bubbles includes a supplemental tube disposed adjacent said sample transport tube and said tubes have ports disposed adjacent one another for submergence in the liquid sample to be analyzed so that, during a cleaning interval, gas bubbles may be flowed through said sample transport tube concurrently with the sample or cleaning liquid for cleaning said sample transport tube and other regions of the analysis sample flow path.

18. The system of claim 17 wherein said control structure for flowing a sample includes a pump that has forward and reverse modes of operation, and said control structure operates said pump in a reverse flow mode during a first part of a spectrometer analysis cycle to remove excess sample material from said analysis region and then in a relatively low forward flow rate mode during a second part of said spectrometer analysis cycle.

19. A process for analyzing liquid sample material such as a lubricating oil comprising the step of:

providing structure defining an analysis region with a polychromater system disposed in sensing relation to said analysis region, said polychromator system including entrance slit structure, exit slit structure composed of a plurality of exit slit regions, and radiation dispersing structure for dispersing radiation passing through said entrance slit structure into a spectrum for application to said exit slit regions, flowing a liquid sample to be analyzed through a sample flow path into said analysis region at a first flow rate, flowing gas bubbles concurrently with said liquid sample for cleaning said sample flow path, reversing the flow direction to remove excess liquid sample from said analysis region, resuming flow in the forward direction at a low flow rate and concurrently subjecting said liquid sample in said analysis region to an electric discharge to excite the liquid sample to spectroemissive levels for sensing by said polychromator system.

20. The process of claim 19 wherein said analysis region includes sample excitation apparatus that includes a pair of spaced metal electrodes, one of said electrodes having an upper surface in spaced juxtaposition to the other electrode and passage structure connected to said inlet of said analysis region, said one metal electrode being disposed with said passage structure extending to an outlet port in said upper surface, structure in said upper surface defining a plurality of channels extending away from said outlet port of said passage structure for discharge of excess quantities of a liquid sample to be analyzed flowed through said passage structure, and the other said electrode having a lower surface of annular configuration in spaced juxtaposition to said upper surface of said one electrode.

21. The process of claim 20 wherein said liquid sample is a lubricating oil material, and said spectrometer system senses metal constituents in said lubricating oil material.

22. The process of claim 20 wherein each said metal electrode contains at least ninety-nine percent silver.

23. The process of claim 19 wherein said relatively low forward flow rate is less than one-half said first flow rate.

* * * * *